United States Patent [19]

Hagiwara et al.

[11] Patent Number: 5,519,316
[45] Date of Patent: May 21, 1996

[54] METHOD AND APPARATUS FOR MEASURING A TONER CONCENTRATION OF A TWO-COMPONENT DEVELOPER

[75] Inventors: Tomoe Hagiwara, Fuji; Mitsuo Aoki, Numazu; Masanori Suzuki, Suntou; Tomio Kondou; Takahisa Kato, both of Numazu, all of Japan

[73] Assignee: Ricoh Company, Ltd., Tokyo, Japan

[21] Appl. No.: 337,438

[22] Filed: Nov. 8, 1994

[30] Foreign Application Priority Data

Nov. 8, 1993 [JP] Japan ................................. 5-302417
Nov. 2, 1994 [JP] Japan ................................. 6-292033

[51] Int. Cl.⁶ ........................... G01N 27/74; G03G 15/08
[52] U.S. Cl. ........................... 324/204; 118/690; 355/208
[58] Field of Search ........................... 324/204; 118/688, 118/689, 690; 355/203, 208, 209

[56] References Cited

U.S. PATENT DOCUMENTS 4,186,341   1/1980   Noguchi et al. ................. 324/204 X
4,519,696   5/1985   Bruyndonckx et al. ........... 324/204 X

FOREIGN PATENT DOCUMENTS 340923   12/1993   Japan ................................. 324/204

Primary Examiner—Gerard R. Strecker
Attorney, Agent, or Firm—Oblon, Spivak, McClelland, Maier & Neustadt

[57] ABSTRACT

In an electrophotographic or electrostatic image forming device, the toner concentration of a two-component developer, i.e., a mixture of toner and carrier is measured on the basis of an output of a magnetic bridge type concentration sensor responsive to the magnetic permeability of the developer. The sensor has a surface whose mean roughness along the center line is less than 0.4 μm Ra.

6 Claims, 3 Drawing Sheets

METHOD AND APPARATUS FOR MEASURING A TONER CONCENTRATION OF A TWO-COMPONENT DEVELOPER

BACKGROUND OF THE INVENTION

The present invention relates to a method of measuring the concentration of toner contained in a two-component developer applicable to a developing device of an electrophotographic electrostatic or image forming apparatus, and an apparatus therefor.

To develop a latent image electrostatically formed on an image carrier, use is made of either a one-component developer, i.e., toner or a two-component developer which is a mixture of toner and carrier. Regarding the two-component developer, toner and carrier are each charged to a particular polarity by being agitated, i.e., by friction. The charged toner develops a latent image, or electrostatic charge image, having been charged to the opposite polarity to the toner. In this connection, in reversal development, the toner deposits on exposed portions. There are available a magnet brush method using iron powder as carrier, a cascade method using beads as carrier, a fur brush method and so forth, which are selectively used in matching relation to the kinds of toner and carrier.

The management of the toner concentration of the developer is vital in insuring high quality and stable images. The toner concentration of the developer is measured by, for example, a magnetic bridge type sensor which is responsive to the magnetic permeability of the developer. A toner concentration is estimated on the basis of a relation between a toner concentration and a sensor output and then fed back. This kind of scheme is disclosed in, for example, Japanese Patent Laid-Open Publication No. 4-24651. However, when the fluidity of the developer stored in a developing device decreases, the developer cannot be agitated stably. As a result, the sensor fails to operate stably and, in the worst case, outputs a signal not representing the actual toner concentration.

SUMMARY OF THE INVENTION

It is, therefore, an object of the present invention to provide a method capable of measuring the toner concentration of a two-component developer accurately, and an apparatus therefor.

In accordance with the present invention, in a method of measuring the toner concentration of a two-component developer by causing it to pass through a sensor portion included in a magnetic bridge type concentration sensor and in terms of magnetic permeability, the sensor has a surface whose mean roughness along the center line is less than 0.4 μm Ra.

Also, in accordance with the present invention, an apparatus for measuring the toner concentration of a two-component developer has a magnetic bridge type concentration sensor for sensing the magnetic permeability of the developer by causing the developer to pass through a sensor portion of the sensor, and a measuring device for measuring a toner concentration on the basis of the magnetic permeability sensed by the sensor. The sensor has a surface whose mean roughness along the center line is less than 0.4 μm Ra.

BRIEF DESCRIPTION OF THE DRAWINGS

The above and other objects, features and advantages of the present invention will become more apparent from the following detailed description taken with the accompanying drawings in which.

DESCRIPTION OF THE PREFERRED EMBODIMENT

Figure 1:
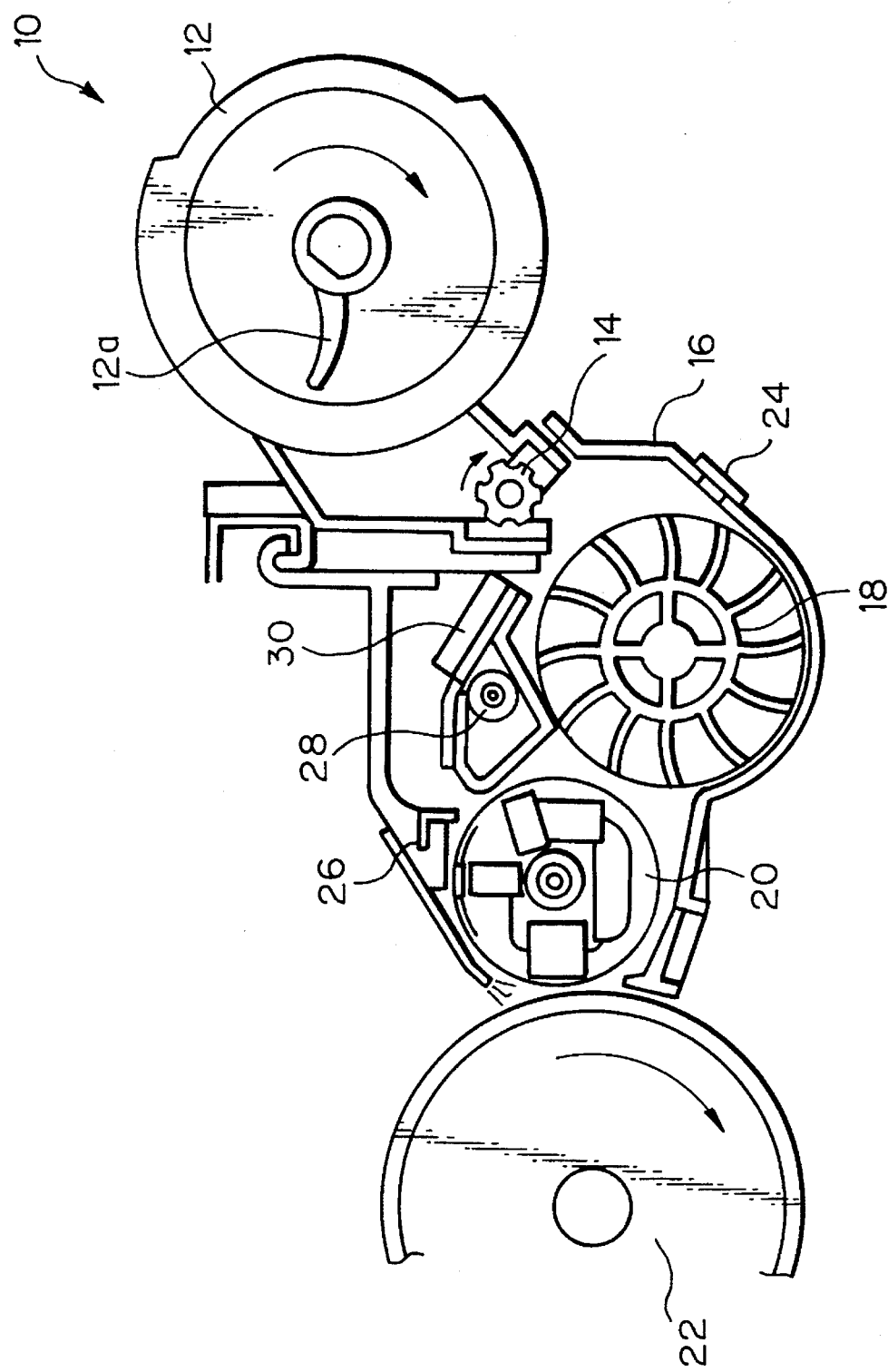
FIG. 1 is a section of a developing device with which the present invention is practicable.

In accordance with the present invention, experiments have shown that a device for measuring the toner concentration of a two-component developer, preferably a magnetic bridge type sensor, should preferably have a mean surface roughness of less than 0.4 μm along the center line thereof. In this connection, a conventional sensor of the kind concerned has a mean surface roughness of 0.4 μm to 0.6 μm Ra along the center line. Such a mean surface roughness equal to or greater than 0.4 μm Ra increases the coefficient of friction between the sensor surface and the developer, so that it takes a substantial period of time for the developer to begin to flow on the sensor surface smoothly. As a result, the sensor output is not stable in the initial stage. The term "Ra" designates the center line average roughness, as described in JIS B-0601 (1994).

On the other hand, in accordance with the present invention, the developer passing through the sensor portion of the sensor should preferably have a volume density of 1.9 g/cm$^3$ to 2.3 g/cm$^3$ when the toner concentration is 2.0 wt %. Volume density greater than 2.3 g/cm$^3$ apparently reduces the volume of the developer and thereby degrades the agitation of the developer. As a result, it takes a substantial period of time for the developer to begin to flow on the sensor surface smoothly, preventing the sensor output from becoming stable in the initial stage. Conversely, volume density smaller than 1.9 g/cm$^3$ apparently increases the volume of the developer and is apt to cause the developing device to overflow. The volume density of the developer has conventionally been 1.8 g/cm$^3$ to 1.9 g/cm$^3$ in the case of ferrite carrier or 2.5 g/cm$^3$ to 4.0 g/cm$^3$ in the case of iron powder carrier.

More desirably, the developer passing through the sensor portion should have a carrier volt, me density ranging from 1.5 g/cm$^3$ to 3.1 g/cm$^3$. Carrier volume density greater than 3.1 g/cm$^3$ apparently reduces the volume of the developer and thereby degrades the agitation of the developer. As a result, it takes a substantial period of time for the developer to begin to flow on the sensor surface smoothly, preventing the sensor output from becoming stable in the initial stage. Carrier volume density smaller than 1.5 g/cm$^3$ apparently increases the volume of the developer and is apt to cause the developing device to overflow.

It is more preferable that the toner of the developer passing through the sensor portion of the sensor has a cohesion degree of 5% to 40%. In this connection, toner in general has a cohesion degree of 5% to 10%. Cohesion degrees higher than 40% degrade the agitation of the developer. As a result, it takes a substantial period of time for the developer to begin to flow on the sensor surface smoothly, preventing the sensor output from becoming stable in the initial stage. Conversely, cohesion degrees lower than 5% cause an excessive amount of toner to be replenished into the developing device. This makes it difficult to deposit a desired amount of charge on the toner and brings about, for example background contamination due to an increase in toner concentration.

Various kinds of toner replenishing methods have been proposed in the past. A large capacity hopper, for example, promotes the effective use of a limited space available in a copier or similar image forming apparatus. In light of this, the large capacity hopper may tie held in a horizontal position and rotated about its own axis to replenish toner. For this type of toner replenishing method, a toner cohesion degree ranging from 5% to 40% is effective.

The toner cohesion degree can be controlled to a desired degree if a small amount of hydrophobic silica is added to the toner. Hence, it is possible to measure toner concentrations accurately without affecting the sensor output.

In accordance with the present invention, while the volume mean particle size of the toner passing through the sensor portion of the sensor is not limited, it should preferably range from 5 μm to 10 μm in respect of image density.

In accordance with the present invention, the mean roughness of the sensor surface along the center line was defined according to Japanese Industrial Standard (JIS) B-0621 and B-0651, while the volume densities of the developer and carrier were measured by a volume density measuring method (JIS Z-2504). Further, to measure the cohesion degree of toner, a powder tester available from Hosokawa Micron (Japan) was loaded with screens of mesh sizes of 150 μm, 75 μm and 45 μm. 2 g of sample toner was put in the top screen, and then the powder tester was caused to vibrate for 30 seconds at an amplitude graduation of 1 mm. Assume:

$$\frac{\text{weight of powder left on top screen}}{\text{amount of collected sample}} \times 100 \quad \text{(a)}$$

$$\frac{\text{weight of powder left on medium screen}}{\text{amount of collected sample}} \times 100 \quad \text{(b)}$$

$$\frac{\text{weight of powder left on bottom screen}}{\text{amount of collected sample}} \times 100 \quad \text{(c)}$$

The cohesion degree (%) was determined by summing up the above (a), (b) and (c).

Hereinafter will be described toner with which the method of the present invention is practicable. A binding resin may be selected from a group of polymers consisting of styrenes including polystyrene, poly-p-chlorostyrene and polyvinyl toluene and their substitutes; and a group of styrene copolymers consisting of styrene-p-chlorostyrene, styrene-propylene, styrene-propylene copolymer, styrene-vinyl toluene copolymer, styrene-vinyl naphthalene copolymer, styrene-methyl acrylate copolymer, styrene-ethyl acrylate copolymer, styrene-methyl methacrylate copolymer, styrene-ethyl methacrylate copolymer, styrene-butyl acrylate copolymer, styrene-octyl acrylate copolymer, styrene-methyl methacrylate, styrene-ethyl methacrylate copolymer, styrene-butyl methacrylate copolymer, styrene-α-methyl chloromethacrylate copolymer, styrene-acrylonitrile copolymer, styrene-vinyl methyl ether copolymer, styrene-vinyl ethyl ether copolymer, styrene-vinyl methylketone copolymer, styrene-butadien copolymer, styrene-isoprene copolymer, styrene-acrylonitrile-indene copolymer, styrene-maleate copolymer, and styrene-ester maleate copolymer.

Any of the following resins may be added to the binding resin: polymethyl methacrylate, polybutyl methacrylate, vinyl polychloride, vinyl polyacetate, polyethylene, polypropylene, polyester, polyurethane, polyamid, epoxy resin, polyvinyl butyral, polyacrylate resin, rosin, modified resin, terpene resin, phenol resin, aliphatic or alicyclic hydrocarbon resin, aromatic petroleum resin, chlorinated paraffin, paraffin wax, etc.

To fix toner images by pressure, use may preferably be made of the following substances (with or without the above resins added thereto): polyolefin (low molecular weight polyethylene, love molecular weight polypropylene, polystyrene oxide, poly-4-ethylene fluoride, etc.), epoxy resin, polyester resin, stylene-butadien copolymer (monomer ratio of 5-30:95-70), olefin copolymer (ethylene-acrylate copolymer, ethylene-ester acrylate copolymer, ethylene-methacrylate copolymer, ethylene-ester methacrylate, ethylene-vinyl chloride copolymer, ethylene-vinyl acetate copolymer or ionomer resin), polyvinyl pyrolydone, methylvinylethermaleic anhydride, malic acid modified phenol resin, phenol modified terpene resin, etc.

For a coloring agent, use may be made of any conventional pigments and dyes alone or in combination. Examples are carbon black, lamp black, iron black, ultramarine, Nigrosine dye, aniline blue, phthalocyanine blue, phthalocyanine green, Hansa Yellow G, Calko Oil Blue, chrome yellow, quinacridone, Benzidine Yellow, Rose Bengal, tryarylmethane dye, and monoazo or diazo pigments.

Additives may be added to the toner applicable to the present invention, as needed. The additives include Teflon, zinc stearic acid and other lubricants, cerium oxide, silicon carbide and other abrasives, aluminum oxide and other fluidity agents, anti-caking agents, carbon black, tin oxide and other conductivity agents, and low molecular weight polyolefin and other fixation promoting agents.

Preferably, the additives should have primary particles whose particles size is smaller than 0.2 μm and whose surfaces are provided with hydrophobic property by a silane coupling agent or silicone oil to a hydrophobic degree of 40% or above. When the hydrophobic degree is less than 40%, moisture is apt to act on the surfaces of the particles in a hot and humid atmosphere, causing the toner to cohere and, therefore, resulting in irregular images. The hydrophobic degree is measured by the methanol wettability method.

A parting agent may be added to the toner applicable to the present invention, if necessary. The parting agent may be, for example, defree fatty acid type carnauba wax, montan-based ester wax or oxidized rice wax. These waxes may be used alone or in combination and should preferably have a concentration of 15 wt % in the entire toner.

The present invention is practicable with any conventional carrier, e.g., iron powder, ferrite powder, nickel powder or similar magnetic powder or glass beads with or without the surface thereof coated with resin.

Examples of the present invention and comparative examples will be described hereinafter.

Figure 2:
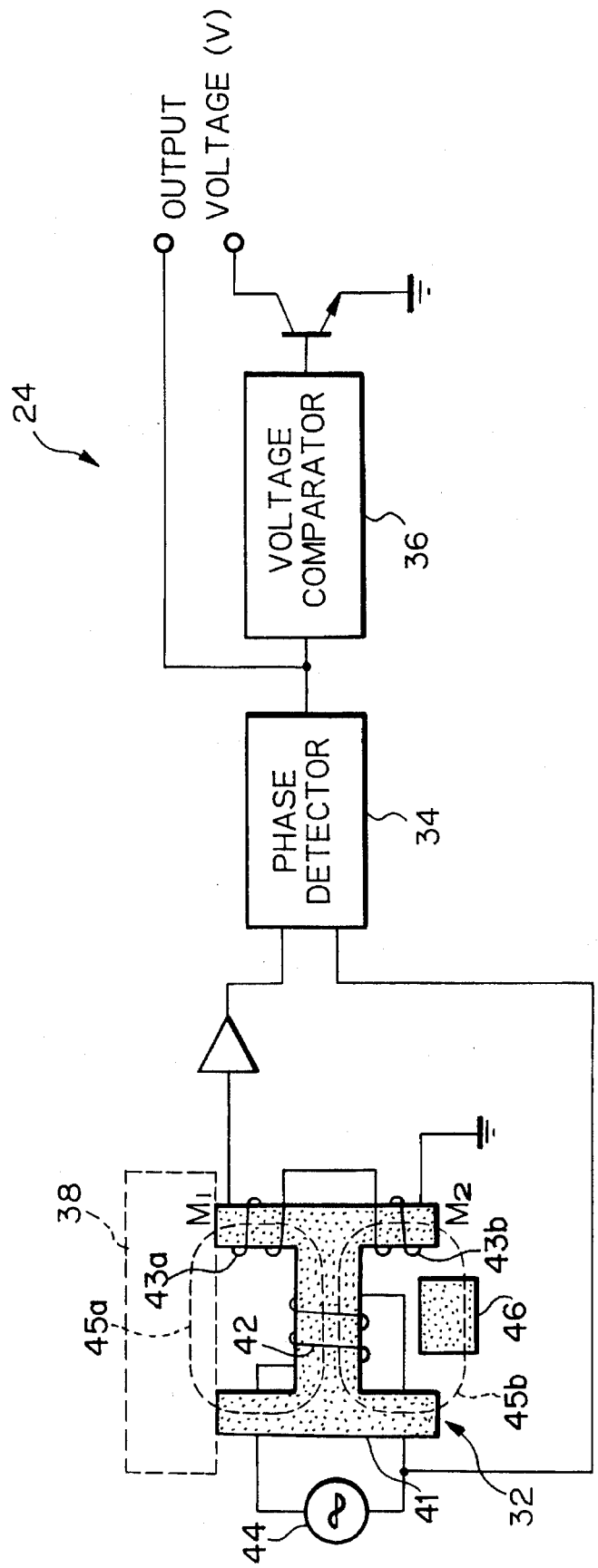
FIG. 2 is a block diagram schematically showing a magnetic bridge type sensor included in the developing device of FIG. 1.
Figure 3:
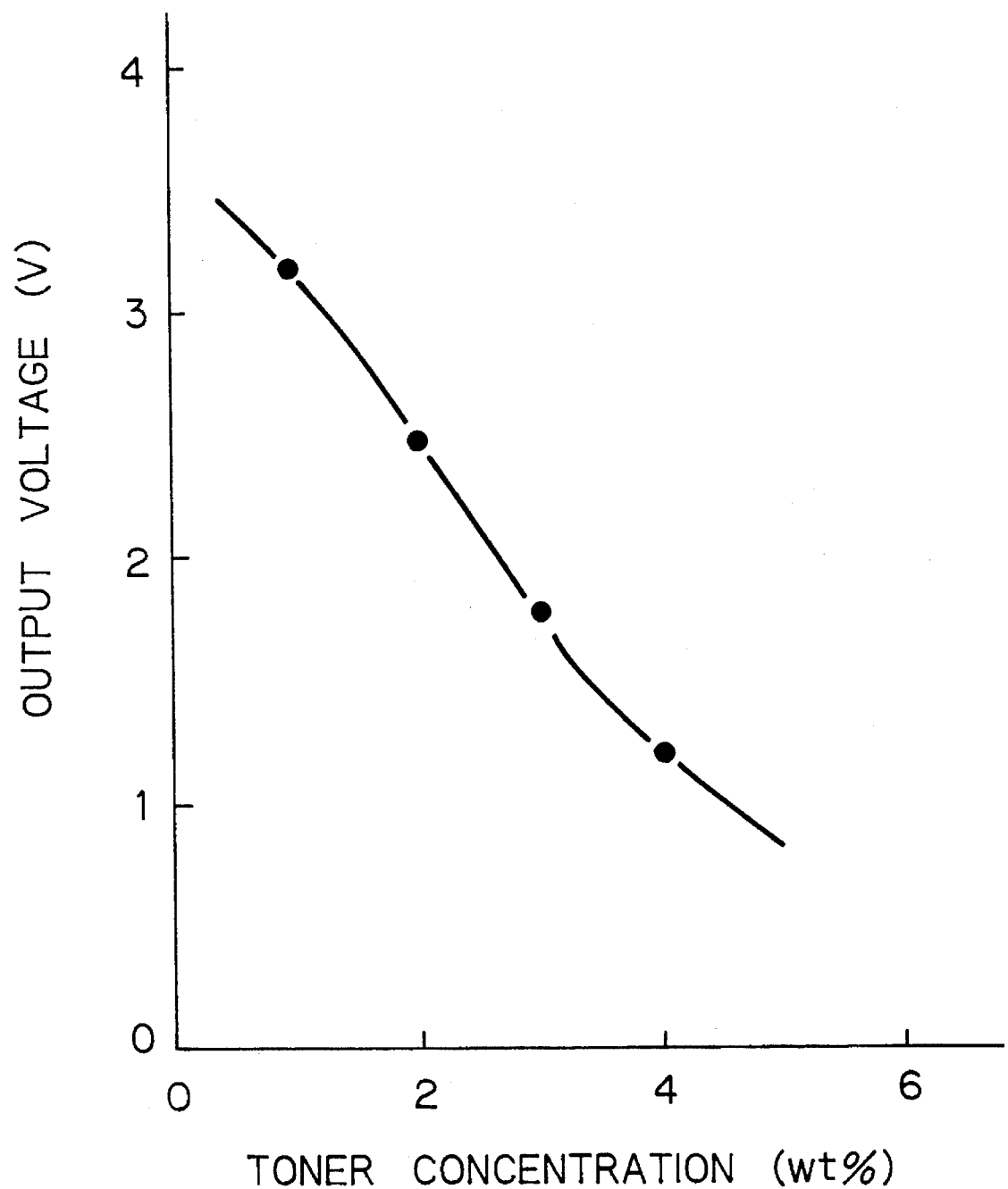
FIG. 3 is a graph indicating a relation between toner concentration and output voltage.

Referring to FIG. 1, a developing device for practicing the present invention is shown and generally designated by the reference numeral 10. As shown, the device 10 has a toner cartridge 12 having an agitator 12a therein. Toner from the cartridge 12 is introduced into a casing 16 via a toner supply roller 14. An agitator in the form of a roller 18 is disposed in the casing 16 and agitates the developer while feeding it to a developing roller 20. The toner deposited on the developing roller 20 in a layer is brought into contact with the surface of a photoconductive drum 22, thereby developing a latent image electrostatically formed thereon. A magnetic bridge type concentration sensor 24 is mounted on part of the outer periphery of the casing 16. There are also shown in the figure a doctor blade 26, a conveyor screw 28, and a separator 30. As shown in FIG. 2, the sensor 24 has a magnetic bridge section 32 having an adjustable ferrite core, a phase detector 34, and a voltage comparator 36. The reference numeral 38 designates the developer. As shown in FIG. 2, a primary winding 42 and secondary windings 43a and 43b are wound around a core 41. The secondary windings 43a and 43b are connected in series such that they generate fluxes opposite in direction to each other. The primary winding 42 is connected to an oscillator 44. A magnetic circuit 45a is held in contact with a developer 38 while a magnetic circuit 45b includes a ferrite core 46 capable of adjusting the flux. In this configuration, as the toner in the developer 38 is consumed, the effective permeability of the developer 38 and, therefore, the mutual inductance $M_1$ of the magnetic circuit 45a varies. The resulting difference between the mutual inductance $M_1$ and the mutual inductance $M_2$ of the other magnetic circuit 45b produces a differential output. The ferrite core 46 is positioned such that the mutual inductances $M_1$ and $M_2$ are equal to each other when the developer has a preselected toner concentration. Then, a relation $M_1 < M_2$ will hold if the actual toner concentration is higher than the preselected value, or a relation $M_1 > M_2$ will hold if the former is lower than the latter. The differential output is amplified and then compared with a reference signal by the phase detector 34. The output of the phase detector 34 is compared with a reference voltage by the voltage comparator 36. The output of the voltage comparator 36 is used to operate a toner replenishing circuit, not shown, for replenishing toner. FIG. 3 is a graph indicating a relation between the output voltage of the sensor 24 and the toner concentration.

[Carrier]

In Example 1 and Comparative Example 1, spherical Fe, Cu, Zn of ferrite having a particle size of about 100 μm was prepared.

In Example 2, the substance used in Example 1 was coated with silicone resin.

In Examples 3, 4, 5 and 6, spherical Fe, Zn or ferrite having a particle size of about 70 μm was coated with silicone resin.

[Toner]

In Examples 1, 2 and 3 and Comparative Example 1, 88 parts by weight of styrene resin, 10 parts by weight of carbon black and 2 parts by weight of quaternary ammonium salt were melted by heat, dispersed, and then classified to produce toner having a mean particle size of about 11 μm.

In Example 4, Example 1 was repeated to produce toner whose mean particle size was about 12 μm.

In Example 5, 0.5 part by weight of silica was applied to 100 parts by weight of the particles produced in Example 4.

In Example 6, 1.0 part by weight of silica was applied to 100 parts by weight of the particles produced in Example 4.

In Example 7, Example 6 was repeated to produce toner having a mean particle size of about 8 μm.

In Example 8, Example 6 was repeated to produce toner having a mean particle size of about 7 μm.

FIG. 3 shows the output of the sensor 24 shown in FIG. 2 and used in relation to the above Examples and Comparative Examples. The mean roughness along the center line is 0.25 μm Ra.

Developers having characteristics listed in Table 1 below were used to measure the output of the sensor 24 when the toner concentration was 1%, 2%, and 3%. Deviations from ideal output voltages are represented by ΔV; "3.2 V", "2.5 V" and "1.8 V" shown in Table 1 are the ideal output voltages.

TABLE 1

| | Mean Roughness (μmRa) | Developer Bulk Density for 2 Wt % of Toner | Carrier Bulk Density | Toner Cohesion Degree (%) | Sensor Output Voltage (V) | | | Δ(V) | | | Toner Particle Size (μm) |
|---|---|---|---|---|---|---|---|---|---|---|---|
| | | | | | 1% 3.2 V | 2% 2.5 V | 3% 1.8 V | 1% | 2% | 3% | |
| Comp. Ex. 1 | 0.60 | 3.7 | 4.5 | 35 | 3.9 | 3.4 | 2.5 | +0.7 | +0.9 | +0.7 | 11 |
| Ex. 1 | 0.25 | 3.7 | 4.5 | 35 | 3.5 | 3.8 | 2.2 | +0.3 | +0.3 | +0.4 | 11 |
| Ex. 2 | 0.25 | 1.2 | 3.5 | 35 | 3.3 | 2.7 | 2.2 | +0.1 | +0.2 | +0.4 | 11 |
| Ex. 3 | 0.25 | 1.9 | 2.7 | 35 | 3.3 | 2.4 | 1.9 | +0.1 | −0.1 | +0.1 | 11 |
| Ex. 4 | 0.25 | 1.9 | 2.7 | 20 | 3.2 | 2.6 | 1.7 | 0.0 | +0.1 | −0.1 | 12 |
| Ex. 5 | 0.25 | 1.9 | 2.7 | 15 | 3.1 | 2.6 | 1.8 | −0.1 | +0.1 | 0.0 | 12 |
| Ex. 6 | 0.25 | 1.9 | 2.7 | 8 | 3.2 | 2.5 | 1.9 | 0.0 | 0.0 | +0.1 | 11 |
| Ex. 7 | 0.25 | 2.0 | 2.7 | 15 | 3.3 | 2.5 | 2.0 | +0.1 | 0.0 | +0.2 | 8 |
| Ex. 8 | 0.25 | 2.0 | 2.7 | 25 | 3.4 | 2.6 | 1.9 | +0.2 | +0.1 | +0.1 | 7 |

In summary, it will be seen that the present invention is capable of measuring the toner concentration of a two-component developer with accuracy by using a magnetic bridge type concentration sensor.

Various modifications will become possible for those skilled in the art after receiving the teachings of the present disclosure without departing from the scope thereof.

What is claimed is:

1. A method of measuring a toner concentration of a two-component developer, comprising the steps of:

(a) passing said two-component developer through a sensor means of a magnetic bridge type concentration sensor, a surface of said sensor means having a center line mean roughness of less than 0.4 μm Ra;

(b) sensing a magnetic permeability of said two-component developer via said sensor means; and (c) measuring a toner concentration of said two-component developer in accordance with the magnetic permeability sensed by said sensor means.

2. A method according to claim 1, wherein said two-component developer comprises toner and carrier, said toner having a mean volume particle size ranging from 5 μm to 10 μm.

3. A method according to claim 2, wherein said two-component developer has a volume density of 1.9 g/cm$^3$ to 2.3 g/cm$^3$ when the toner concentration is 2.0 wt. %.

4. A method according to claim 2, wherein said carrier has a volume density of 1.5 g/cm$^3$ to 3.1 g/cm$^3$.

5. A method according to claim 2, wherein said toner has a cohesion degree in a range of 10% to 30%.

6. An apparatus for measuring a toner concentration of a two-component developer, comprising:

a magnetic bridge type concentration sensor for sensing a magnetic permeability of said two-component developer by passing said two-component developer through a sensor means thereof, said sensor means having a surface whose center line mean roughness is less than 0.4 μm Ra; and measuring means, connected to said sensor means, for measuring a toner concentration on the basis of said magnetic permeability sensed by said sensor means.

* * * * *